US010059605B1

(12) United States Patent
Saha (10) Patent No.: US 10,059,605 B1
(45) Date of Patent: Aug. 28, 2018

(54) PROCESS FOR USING PHYTOCHEMICALS AND SUGAR ACIDS TO CREATE ONE OR MORE ENGINEERED MEDIA FOR USE IN A WATER PURIFICATION FILTER

(71) Applicant: Anuj K Saha, Martinez, GA (US)

(72) Inventor: Anuj K Saha, Martinez, GA (US)

( * ) Notice: Subject to any disclaimer, the term of this patent is extended or adjusted under 35 U.S.C. 154(b) by 0 days.

(21) Appl. No.: 15/938,228

(22) Filed: Mar. 28, 2018

Related U.S. Application Data

(63) Continuation-in-part of application No. 14/834,891, filed on Aug. 25, 2015, now Pat. No. 9,963,367.

(51) Int. Cl.
| | |
|---|---|
| *C02F 1/68* | (2006.01) |
| *C02F 1/28* | (2006.01) |
| *B01J 20/20* | (2006.01) |
| *B01J 20/16* | (2006.01) |
| *B01J 20/02* | (2006.01) |
| *B01J 20/28* | (2006.01) |
| *B01J 20/32* | (2006.01) |
| *A61L 2/238* | (2006.01) |
| *C02F 101/20* | (2006.01) |
| *C02F 101/36* | (2006.01) |
| *C02F 101/34* | (2006.01) |
| *C02F 101/00* | (2006.01) |
| *C02F 101/16* | (2006.01) |
| *C02F 101/14* | (2006.01) |

(52) U.S. Cl.
CPC ............... *C02F 1/28* (2013.01); *A61L 2/238* (2013.01); *B01J 20/0233* (2013.01); *B01J 20/165* (2013.01); *B01J 20/20* (2013.01); *B01J 20/28007* (2013.01); *B01J 20/28026* (2013.01); *B01J 20/3204* (2013.01); *B01J 20/3214* (2013.01); *B01J 20/3236* (2013.01); *C02F 1/68* (2013.01); *C02F 1/281* (2013.01); *C02F 1/283* (2013.01); *C02F 1/286* (2013.01); *C02F 2101/006* (2013.01); *C02F 2101/14* (2013.01); *C02F 2101/163* (2013.01); *C02F 2101/20* (2013.01); *C02F 2101/345* (2013.01); *C02F 2101/363* (2013.01); *C02F 2101/366* (2013.01); *C02F 2303/04* (2013.01); *C02F 2305/08* (2013.01)

(58) Field of Classification Search
CPC ........ B01J 19/00; B01J 20/00; B01J 20/0233; B01J 20/20
USPC .................................................. 502/400–439
See application file for complete search history.

*Primary Examiner* — Daniel McCracken
(74) *Attorney, Agent, or Firm* — James Carson (57) ABSTRACT

The process for creating one or more engineered media for use in a water purification filter is a passive multi-stage multi-media filter for use in water purification. The process for creating one or more engineered media for use in a water purification filter removes harmful contaminants from a water stream including, but not limited to, toxic heavy metals and metalloids, pharmaceutical residues, micro-toxins, endocrine disrupters, chlorinated and other halogenated solvents, fluoride, nitrate, and naturally occurring radioactive contaminants. The process for creating one or more engineered media for use in a water purification filter maintains concentrations of phytochemicals that provide health benefits. Water processed through the process for creating one or more engineered media for use in a water purification filter meets United States, European Union and World Health Organization standards for safe drinking water.

20 Claims, 3 Drawing Sheets

PROCESS FOR USING PHYTOCHEMICALS AND SUGAR ACIDS TO CREATE ONE OR MORE ENGINEERED MEDIA FOR USE IN A WATER PURIFICATION FILTER

CROSS REFERENCES TO RELATED APPLICATIONS

This non-provisional application claims priority under 35 USC 120 to United States non-provisional application U.S. Ser. No. 14/834,891 filed on Aug. 25, 2015, by the inventor: Anuj K. Saha of Martinez, Ga.

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of chemical/biochemical processes including sorbent compositions, more specifically, a process for preparing a filter media.

SUMMARY OF INVENTION

The process for creating one or more engineered media for use in a water purification filter creates filter media for a passive multi-stage multi-media filter used in water purification. In the first potential embodiment of the disclosure, the passive multi-stage multi-media filter used in water purification will be marketed as the Guru-Brahma filter. The process for creating one or more engineered media for use in a water purification filter created engineered media that remove harmful contaminants from a water stream including, but not limited to, toxic heavy metals and metalloids, pharmaceutical residues, micro-toxins, endocrine disrupters, chlorinated and other halogenated solvents, and naturally occurring radioactive contaminants. The process for creating one or more engineered media for use in a water purification filter simultaneously releases concentrations of beneficial phytochemicals including, but not limited to flavonoids, phytosterols, tannins, polysaccharides, saponins, polyacetylenes, and keeps in close contact with metallic nanoparticles of a noble metal that provide many health benefits including natural cleansing of the blood and the liver and protection against the accumulation of bacteria, fungus, and viruses. The noble metal is selected from the group consisting of silver and gold. Water processed through the process for creating one or more engineered media for use in a water purification filter meets United States, European Union and World Health Organization standards for safe drinking water.

These together with additional objects, features and advantages of the process for creating one or more engineered media for use in a water purification filter will be readily apparent to those of ordinary skill in the art upon reading the following detailed description of the presently preferred, but nonetheless illustrative, embodiments when taken in conjunction with the accompanying drawings.

In this respect, before explaining the current embodiments of the process for creating one or more engineered media for use in a water purification filter in detail, it is to be understood that the process for creating one or more engineered media for use in a water purification filter is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the process for creating one or more engineered media for use in a water purification filter.

It is therefore important that the claims be regarded as including such equivalent construction insofar as they do not depart from the spirit and scope of the process for creating one or more engineered media for use in a water purification filter. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Figure 1:
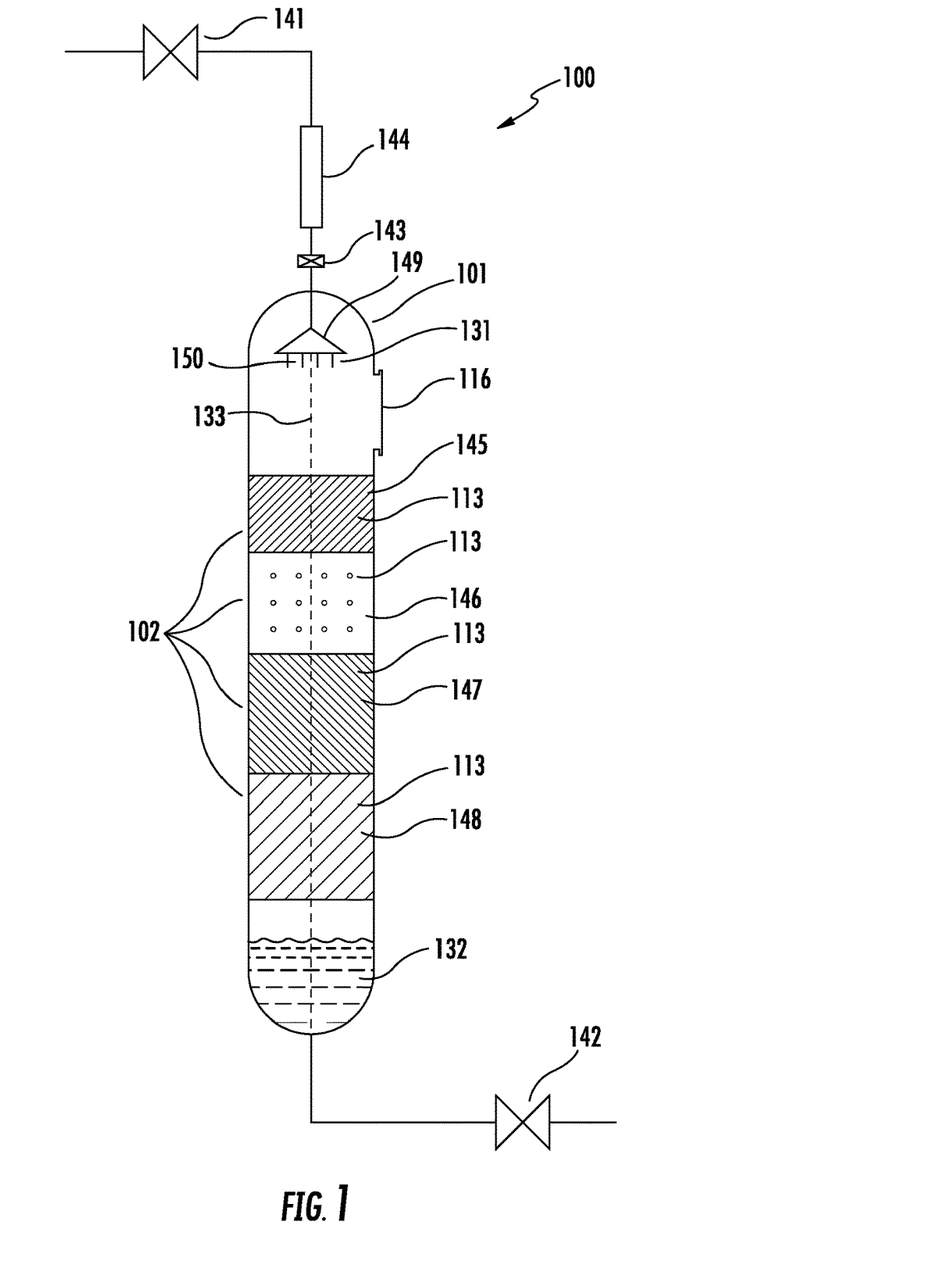
FIG. 1 is a front view of an embodiment of the disclosure.
Figure 2:
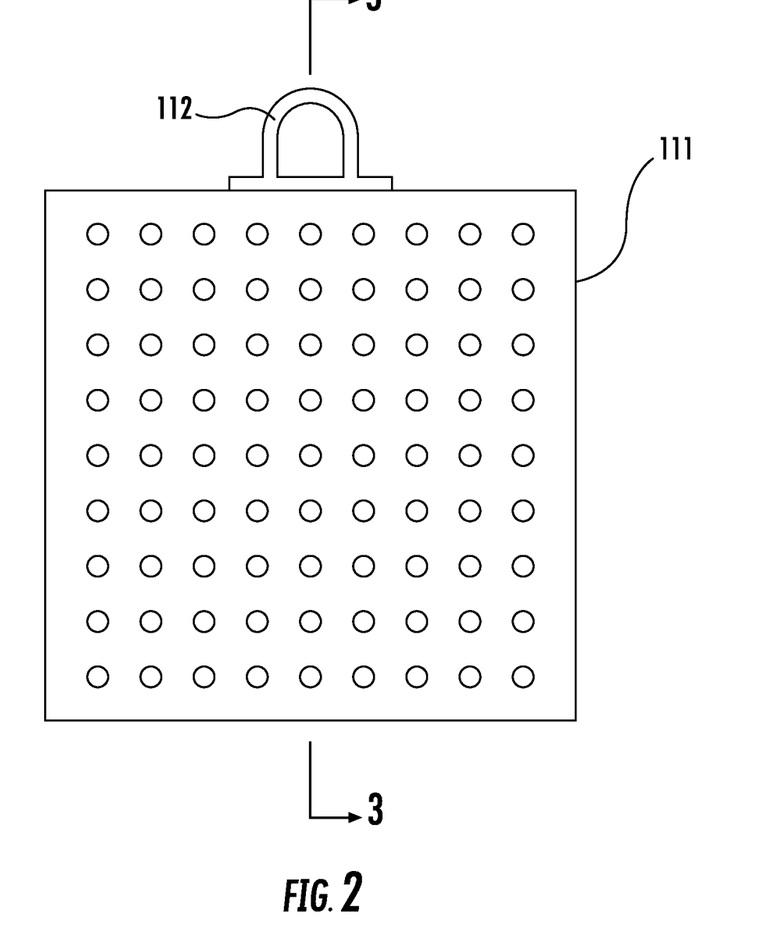
FIG. 2 is a detail view of one of the plurality of filter modules used in an embodiment of the disclosure.
Figure 3:
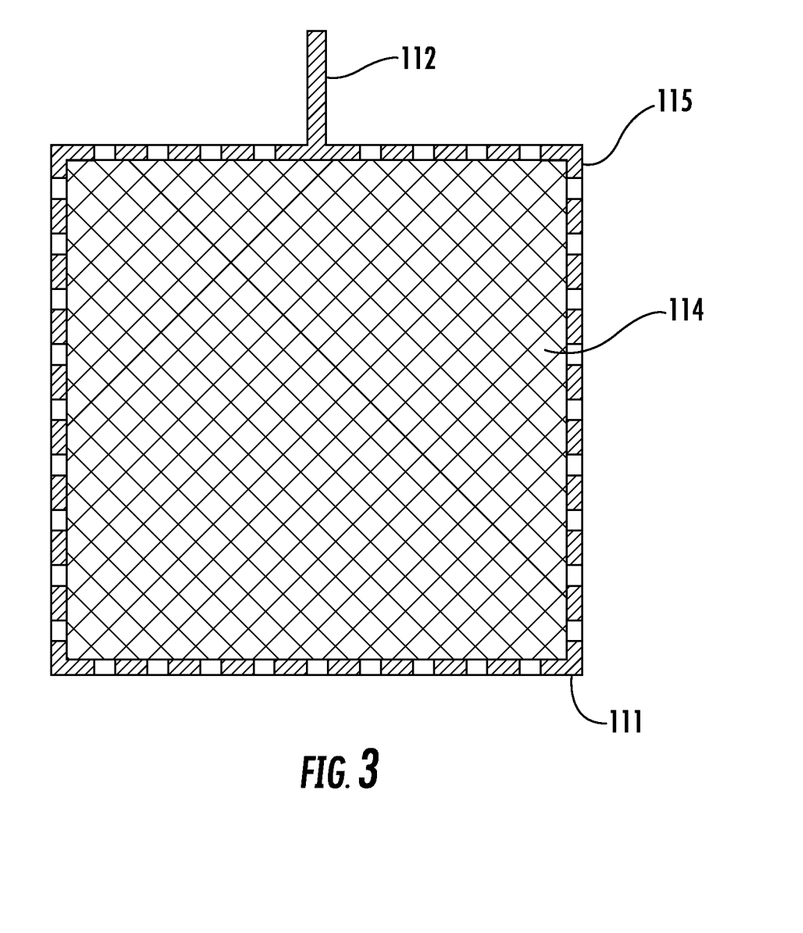
FIG. 3 is a cross-sectional view of one of the plurality of filter modules used in an embodiment of the disclosure across 3-3.

Detailed reference will now be made to a first potential embodiment of the disclosure, which is illustrated in FIGS. 1 through 3.

The water filter 100 (hereinafter invention) comprises a filter housing 101 and a plurality of filter modules 102.

The filter housing 101 is a column which contains the plurality of filter modules 102 and through which untreated water 131 is passed. Each of the plurality of filter modules 102 are stacked within the filter housing 101 such that that the untreated water 131 must pass through each of the plurality of filter modules 102 in order to pass through the filter housing 101. The purpose of each of the plurality of filter modules 102 is to remove contaminants from the untreated water 131 so that the treated water, hereinafter referred to as drinking water 132, is safe for human consumption. The filter housing 101 is further formed with an access port 116 that is used for the installation and replacement of the plurality of filter modules 102. The plurality of filter modules 102 are discussed elsewhere in this disclosure. The filter housing 101 can be made of several materials including, but not limited to, composite fiberglass, polycarbonate or polyacrylic.

It is explicitly acknowledged that the untreated water 131 can be mechanically pumped through the filter housing 101. However, the specification and claims of this disclosure will hereinafter implicitly assume that the flow of untreated water 131 through filter housing 101 and the plurality of filter modules 102 will be due to gravitational forces. This is done for the purposes of simplicity and clarity of exposition of the disclosure is not intended to limit the scope of the disclosure or the appended claims. Those skilled in the art will recognize that the disclosure can be readily modified to accommodate mechanical pumps to pump untreated water 131 through the filter housing 101.

The purpose of the plurality of filter modules 102 is to remove contaminants from the untreated water 131 so that the drinking water 132, is safe for human consumption. As untreated water 131 flows through the filter housing 101, the invention 100 is able to remove the following contaminants: 1) toxic heavy metals and metalloids including, but not limited to, arsenic (As), mercury (Hg), cadmium (Cd), lead (Pb), copper (Cu) and zinc (Zn); 2) pharmaceutical residues, micro-toxins and endocrine disrupters including, but not limited to, PCBs, DDT, Dioxin, Bis-Phenol, Bis-Phthalate; 3) chlorinated and other halogenated solvents including, but not limited to, trichloroethylene and perchloroethylene (tetrachloroethylene); 4) naturally occurring radioactive contaminants including, but not limited to, uranium (U) and radium (Ra); and, 5) other contaminants including, but not limited to, fluoride (F) and nitrate (NO3).

While removing the above contaminants, the plurality of filter modules 102 also release beneficial phytochemicals including, but not limited to, flavanoids, phytosterols, tannins, polysaccharides, saponins and polyacetylenes that provide many health benefits including natural cleansing and detoxification for the blood and the liver. Some of these phytochemicals along with nanoparticles of embedded noble metals selected from the group consisting of silver (Ag) and gold (Au), provide protection against accumulation of bacteria, fungus, virus, microbes and prevent inflammation of cells and tissues.

Each of the plurality of filter modules 102 further comprises a cancellated package 111, a lifting lug 112 and an individual filtering medium 114 selected from a plurality of filtering mediums 113. The cancellated package 111 is a textile 115 structure that is used to contain an individual filtering medium 114. The textile 115 used to create the cancellated package 111 is designed with a mesh that allows water to pass through the textile 115 while containing the individual filtering medium 114 contained within the cancellated package 111. The cancellated package 111 has attached to it a lifting lug 112. The lifting lug 112 is a commercially available webbing that is used to form a handle that can be used to carry and position the cancellated package 111 within the filter housing 101. The individual filtering medium is a composition of matter that interacts with the untreated water 131 as it passes through the filter housing 131 to remove specific contaminants and release phytochemicals as well as to keep the untreated water 131 in close contact with embedded nanoparticles of noble metals selected from the group consisting of silver (Ag) and gold (Au). In the first potential embodiment of the disclosure, the textile 115 is a 50 mesh polypropylene fabric structured in the form of a simple sack. The lifting lug 112 is sewn directly onto the polypropylene fabric. The plurality of filtering mediums 113 are discussed elsewhere in this disclosure.

The shape of each of the plurality of filter modules 102 is designed to completely cover the cross-section of the filter housing 101 when the cross-section is cut at a right angle relative to the primary axis 133 of the filter housing 101. The inner diameter of the filter housing 101 is selected such that at normal flow of operation the pressure drop across the plurality of filter modules 102 remains less than 4 psi.

The plurality of filtering mediums 113 further comprises cleaned burdock roots, nanosilver or nanogold embedded activated carbon, nanosilver or nanogold embedded natural zeolite, and nanosilver or nanogold embedded activated bone char. Each of these filtering mediums are discussed below.

Cleaned burdock root (hereinafter CBR) are the chopped and cleaned roots of the burdock plant having particle size range of 3.0 mm to 4.5 mm. The primary composition (up to 50%) of the burdock root is inulin. Inulin is a polysaccharide having a molecular formula of $C_{228}H_{382}O_{191}$. Inulin boosts the immune system and eliminates bacterial pathogens. Inulin is a scavenger for micro-toxins and heavy metals such as mercury (Hg), cadmium (Cd), and arsenic (As). Besides inulin, the Burdock root contains several flavanoid anti-oxidants, tannins and a polyacetylene name arctiin ($C_{27}H_{34}O_{11}$). Arctiin is an anti-viral and anti-inflammatory agent. Micro toxins and the toxic heavy metals (As, Hg, Cd) are removed from the untreated water 131 through contact with the CBR. CBR removes some pharmaceutical residues as well. CBR releases several phytochemicals that prevent the accumulation of bacteria, virus, or pathogens and enriches the water to boost the immune system and the ability to fight inflammation. Some of the phytochemicals contained within the CBR are highly reactive with oxidizing agents. This high reactivity causes the phytochemicals contained with the CBR to scavenge for oxidizing agents that would otherwise oxidize the embedded nanoparticles of noble metals selected from the group consisting of silver (Ag) and gold (Au). This helps to keep the selected nanoparticles of noble metals in a reduced state and improves the effectiveness of the selected embedded nanoparticles of noble metals in providing protection against accumulation of bacteria, fungus, virus, microbes and preventing inflammation of cells and tissues.

The structure of this disclosure will initially assume that the specific noble metal used for the nanoparticle selected from the group consisting of silver (Ag) and gold (Au) is silver (Ag). This assumption is made strictly for clarity and simplicity and is not meant to limit the specification or claims presented in this disclosure. The use of gold (Au) for the purposes described in this disclosure are disclosed in subsequent passages in this disclosure.

Cleaned burdock root is a well-known and documented bio-reduction agent that performs several chemical functions within this disclosure. The ready availability and high oxygen radical absorbance capacity (ORAC) of the chopped burdock root makes cleaned burdock a natural choice for the purposes of this disclosure. The applicant explicitly notes that several bio-reducing agents with equal or superior performance for the purposes described in this disclosure exist. The structure of this disclosure will initially assume the use of chopped burdock root as the bio-reducing agent for in this disclosure. This assumption is made strictly for clarity and simplicity and is not meant to limit the specification or claims presented in this disclosure. The use of alternate bio-reducing agents for the purposes described in this disclosure are disclosed in subsequent passages in this disclosure.

Nanosilver embedded activated carbon (hereinafter NSEAC) is an engineered media. The preparation of NSEAC is discussed elsewhere in this disclosure. The NSEAC is granular in structure with an average particle size range between 15 to 20 mesh. The NSEAC filter media will capture the endocrine disrupters, the chlorinated and other halogenated solvents, and naturally occurring radium (Ra) from the untreated water. The NSEAC will also remove the remaining levels of pharmaceutical compounds and micro toxins that are not captured up by the CBR. The presence of metallic nanosilver in the NSEAC is a second measure that prevents the accumulation of bacteria, virus, or pathogens within the invention 100 and the drinking water 132.

Nanosilver embedded natural zeolite (hereinafter NSENZ) is an engineered media. The preparation of NSENZ is discussed elsewhere in this disclosure. The NSENZ has an average particle size range between 15 to 20 mesh. Chabazite, Mordenite, or Clinoptilolite are the preferred choices as the natural zeolite substrate. The NSENZ filter media will remove lead (Pb), copper (Cu) and zinc (Zn) contamination from the water stream. The presence of metallic nanosilver in the NSENZ is an additional measure that prevents the accumulation of bacteria, virus, or pathogens within the invention 100 and the drinking water 132.

Nanosilver embedded activated bone char (hereinafter NSEBC) is an engineered media. The preparation of NSEBC is discussed elsewhere in this disclosure. The NSEBC has an average particle size of between 15 to 20 mesh. The NSEBC filter media removes contaminants such as uranium (U), fluoride (F), and nitrate (NO3) from the untreated water stream 131. The NSEBC will also remove the remaining levels of any trace quantities of arsenic (As), cadmium (Cd), and mercury (Hg) that were not removed by the CBR.

Untreated water that is treated by the plurality of filtering mediums 113 described above will be free from all contaminants and will meet the primary drinking water standards defined by the United States Environmental Protection Agency, the World Health Organization, and the European Union and which are specifically described elsewhere in this disclosure.

The order of the plurality of filtering mediums 113 through which the untreated water 131 flows does not impact the effectiveness of the water treatment. The selection of the individual filtering mediums 114 can be varied based on knowledge of the contamination contained in the untreated water 131. For example, if it is known that the untreated water does not contain unacceptable levels of lead (Pb), copper (Cu), or zinc (Zn) then a filter module containing NSENZ does not need to be selected for use in the invention 100. Similarly, if it is known that the untreated water contains unusually high levels of naturally occurring uranium (U), more than one filter module containing NSEBC can be used in the invention 100.

In the first potential embodiment of the disclosure, the invention 100 is assembled and operates as follows.

The plurality of filter modules 113 comprises a fifth CBR filter module 145, a sixth NSEAC filter module 146, a seventh NSENZ filter module 147, and an eighth NSEBC filter module 148. The access port 116 is opened and the plurality of filter modules 113 are placed into the filter housing in the following order: the eighth NSEBC filter module 148, the seventh NSENZ filter module 147, the sixth NSEAC filter module 146, and finally the fifth CBR filter module 145. The access port 116 is then closed.

Untreated water 131 flows through a first inlet valve 141 which feeds the untreated water 131 into a fourth in-line filter cartridge 144. The fourth in-line filter cartridge 144 is a 5 micron filter that removes particulates from the untreated water 131. The untreated water 131 then flows through a third isolation valve 143. The purpose of the third isolation valve 143 is to provide a way to shut off water flow between the fourth in-line filter cartridge 144 and the filter housing 101 so that the fourth in-line filter cartridge 144 can be replaced. The untreated water 131 then flows into the filter housing 101 and through a ninth spray nozzle 149. The purpose of the ninth spray nozzle 149 is to distribute the untreated water 131 in a tenth water spray 150 evenly across the cross-section of the filter housing 101 as described above. The untreated water 131 then flows through the plurality of filter modules 102 for processing. Drinking water 132 is withdrawn from the filter housing through a second outlet valve 142.

The preferred method for the preparation of 1 kilogram of the NSEAC filter media is a bio-reduction method described below.

1) Prepare 1.5 lit of 1 Molar silver nitrate (AgNO3) solution by dissolving 1.5 gm-mole of AgNO3 in 1.5 liters of potable water. Keep the solution covered and away from sunlight.

2) Take 300 gm of clean organic chopped Burdock Root and add 1.5 liters of warm (65 C) potable water. Stir well and soak the roots for 4 hours. Filter the contents to remove the solids from the burdock root extract. Cover the burdock root extract and set it aside.

3) Place 1 Kg of granular activated carbon (particle size 15 to 20 mesh) in a 5 gal tumbler.

4) Add 1.5 liters of 1 Molar AgNO3 solution to the tumbler and tumble for 60 minutes at low speed;

5) Add 1.5 liters burdock root extract and tumble for 3 hours at low speed.

6) Keep the contents of the tumbler covered and allow it to sit for 20 to 24 hours in the absence of light.

7) Changes in the color of the fluid inside the tumbler will indicate bio-reduction of AgNO3 to nanosilver particles embedded within the structure of the activated carbon matrix.

8) Samples of embedded carbon can be drawn from the tumbler, monitored and measured using an ultraviolet visible spectrophotometer.

9) Following bio-reduction and confirmation for deposition of the nanoparticles, the contents of the tumbler (NSEAC) is drained from the liquids and washed 3 times with de-ionized water.

10) The washed NSEAC is dried under vacuum to remove the moisture.

11) Depending on the size and uniformity of the embedded nanoparticles, the steps for synthesis may have to be repeated to obtain the desired product.

The methodology described above will produce silver nanoparticles in the size range of 1 to 5 nm (nanometer). The size of the nanoparticles can be altered by varying the strength of the burdock root extract. UV spectrophotometer measurements will confirm that the nanoparticles of silver have been embedded within the matrix of the activated carbon.

The preferred method for the preparation of 1 kilogram of the NSENZ filter media is a bio-reduction method described below.

1) Prepare 1.5 lit of 1 Molar silver nitrate (AgNO3) solution by dissolving 1.5 gm-mole of AgNO3 in 1.5 liters of potable water. Keep the solution covered and away from sunlight.

2) Take 300 gm of clean organic chopped Burdock Root and add 1.5 liters of warm (65 C) potable water. Stir well and soak the roots for 4 hours. Filter the contents to remove the solids from the burdock root extract. Cover the burdock root extract and set it aside.

3) Place 1 Kg of natural zeolite (particle size 15 to 20 mesh) in a 5 gal tumbler.

4) Add 1.5 liters of 1 Molar AgNO3 solution to the tumbler and tumble for 60 minutes at low speed.

5) Add 1.5 liters burdock root extract and tumble for 3 hours at low speed.

6) Keep the contents of the tumbler covered and allow it to sit for 20 to 24 hours in the absence of light;

7) Changes in the color of the fluid inside the tumbler will indicate bio-reduction of AgNO3 to nanosilver particles embedded within the structure of the natural zeolite.

8) Samples of natural zeolite can be drawn from the tumbler, monitored and measured using an ultraviolet visible spectrophotometer.

9) Following bio-reduction and confirmation for deposition of the nanoparticles, the contents of the tumbler (NSENZ) is drained from the liquids and washed 3 times with de-ionized water.

10) The washed NSENZ is dried under vacuum to remove the moisture.

11) Depending on the size and uniformity of the embedded nanoparticles, the steps for synthesis may have to be repeated to obtain the desired product.

The methodology described above will produce silver nanoparticles in the size range of 1 to 5 nm (nanometer). The size of the nanoparticles can be altered by varying the strength of the burdock root extract. UV spectrophotometer measurements will confirm that the nanoparticles of silver have been embedded within the matrix of the natural zeolite.

The preferred method for the preparation of 1 kilogram of the NSEBC filter media is a bio-reduction method described below.

1) Prepare 1.5 lit of 1 Molar silver nitrate (AgNO3) solution by dissolving 1.5 gm-mole of AgNO3 in 1.5 liters of potable water. Keep the solution covered and away from sunlight.

2) Take 300 gm of clean organic chopped Burdock Root and add 1.5 liters of warm (65 C) potable water. Stir well and soak the roots for 4 hours. Filter the contents to remove the solids from the burdock root extract. Cover the burdock root extract and set it aside.

3) Place 1 Kg of activated bone char (particle size 15 to 20 mesh) in a 5 gal tumbler.

4) Add 1.5 liters of 1 Molar AgNO3 solution to the tumbler and tumble for 60 minutes at low speed.

5) Add 1.5 liters burdock root extract and tumble for 3 hours at low speed.

6) Keep the contents of the tumbler covered and allow it to sit for 20 to 24 hours in the absence of light.

7) Changes in the color of the fluid inside the tumbler will indicate bio-reduction of AgNO3 to nanosilver particles embedded within the structure of the activated bone char.

8) Samples of natural zeolite can be drawn from the tumbler, monitored and measured using an ultraviolet visible spectrophotometer.

9) Following bio-reduction and confirmation for deposition of the nanoparticles, the contents of the tumbler (NSEBC) is drained from the liquids and washed 3 times with de-ionized water.

10) The washed NSEBC is dried under vacuum to remove the moisture.

11) Depending on the size and uniformity of the embedded nanoparticles, the steps for synthesis may have to be repeated to obtain the desired product.

The methodology described above will produce silver nanoparticles in the size range of 1 to 5 nm (nanometer). The size of the nanoparticles can be altered by varying the strength of the burdock root extract. UV spectrophotometer measurements will confirm that the nanoparticles of silver have been embedded within the matrix of the activated bone char.

An alternate method for the filter medias embedded with nanoparticles of embedded noble metals selected from the group consisting of silver (Ag) and gold (Au) that are described in this disclosure comprises the use of an organometallic reduction method. Specifically, an organic reducing agent, such as an organic acid, feeds the noble metals selected from the group consisting of silver (Ag) and gold (Au) with the electrons necessary to reduce the selected noble metal.

The structure of this disclosure will assume that the specific organic reducing agent is a sugar acid. Suitable sugar acids include, but are not limited to, glucaric acid, gluconic acid, glyceric acid, and ascorbic acid. Suitable sugar acids would further include, but are not limited to, the following families of sugar acids: ulosonic acid, uronic acid, and aldaric acid. This assumption is made strictly for clarity and simplicity and is not meant to limit the specification or claims presented in this disclosure and will be relaxed in subsequent passages in this disclosure. The assumptions made in this disclosure regarding the use of silver (Au) and the use of burdock root are maintained and will be relaxed in subsequent passages in this disclosure.

An alternate method for the preparation of 1 kg of NSEAC filter media is a combination of sugar acid scavenging/sequestering and pyrolysis (thermal reduction) method described below.

1) Prepare 2 liters of 1 Molar silver nitrate (AgNO3) solution by adding 2 gm-mole of AgNO3 in 2.0 liters of potable water. Cover the contents and keep it away from sunlight;

2) Take 2 gm-mole of sugar acid and dissolve in the 2.0 liter AgNO3 solution. The sugar acid will sequester the silver ions from the solution.

3) Place 1 Kg of activated carbon (particle size 15 to 20 mesh) in a 5 gal tumbler.

4) Add the AgNO3-sugar acid solution to the activated carbon and gently tumble for 3 hours.

5) Allow the activated carbon to settle at the bottom of the tumbler.

6) Drain the fluids from the top of the tumbler and wash the activated carbon 3 times with de-ionized water.

7) Drain the wash water and remove any excess fluid from the activated carbon.

8) Place the activated carbon in a rotary vacuum pyrolyzer and pyrolyze (thermally reduce) the contents for 2 hours at 250 C. The pyrolysis will break the sugar acid's structure and free the sequestered silver ions and embed it within the matrix of the activated carbon as nanoparticles of silver.

Samples of the activated carbon, following pyrolysis, must be analyzed using a UV visible spectrophotometer to measure the size of the silver nanoparticles and check the uniformity of distribution within the carbon matrix. Depending on the results of the analysis, the steps for synthesis may be repeated to obtain the desired NSEAC product.

An alternate method for the preparation of 1 kg of NSENZ filter media is a combination of sugar acid scavenging/sequestering and pyrolysis method described below.

1) Prepare 2 liters of 1 Molar silver nitrate (AgNO3) solution by adding 2 gm-mole of AgNO3 in 2.0 liters of potable water. Cover the contents and keep it away from sunlight;

2) Take 2 gm-mole of sugar acid and dissolve in the 2.0 liter AgNO3 solution. The sugar will sequester the silver ions from the solution.

3) Place 1 Kg of natural zeolite (particle size 15 to 20 mesh) in a 5 gal tumbler;

4) Add the AgNO3-sugar acid solution to the natural zeolite and gently tumble for 3 hours.

5) Allow the natural zeolite to settle at the bottom of the tumbler.

6) Drain the fluids from the top of the tumbler and wash the natural zeolite 3 times with de-ionized water.

7) Drain the wash water and remove any excess fluid from the natural zeolite.

8) Place the natural zeolite in a rotary vacuum pyrolyzer and pyrolyze the contents for 2 hours at 250 C. The pyrolysis will break the sugar acid's structure and free the sequestered silver ions and embed it within the matrix of the natural zeolite as nanoparticles of silver.

Samples of the natural zeolite, following pyrolysis, must be analyzed using a UV visible spectrophotometer to measure the size of the silver nanoparticles and check the uniformity of distribution within the natural zeolite. Depending on the results of the analysis, the steps for synthesis may be repeated to obtain the desired NSENZ product.

An alternate method for the preparation of 1 kg of NSEBC filter media is a combination of sugar acid scavenging/sequestering and pyrolysis method described below.

1) Prepare 2 liters of 1 Molar silver nitrate (AgNO3) solution by adding 2 gm-mole of AgNO3 in 2.0 liters of potable water. Cover the contents and keep it away from sunlight;

2) Take 2 gm-mole of sugar acid and dissolve in the 2.0 liter AgNO3 solution. The sugar acid will sequester the silver ions from the solution.

3) Place 1 Kg of activated bone char (particle size 15 to 20 mesh) in a 5 gal tumbler;

4) Add the AgNO3-sugar acid solution to the activated bone char and gently tumble for 3 hours.

5) Allow the activated bone char to settle at the bottom of the tumbler.

6) Drain the fluids from the top of the tumbler and wash the activated bone char 3 times with de-ionized water.

7) Drain the wash water and remove any excess fluid from the activated bone char.

8) Place the activated bone char in a rotary vacuum pyrolyzer and pyrolyze the contents for 2 hours at 250 C. The pyrolysis will break the sugar acid's structure and free the sequestered silver ions and embed it within the matrix of the activated bone char as nanoparticles of silver.

Samples of the activated bone char, following pyrolysis, must be analyzed using a UV visible spectrophotometer to measure the size of the silver nanoparticles and check the uniformity of distribution within the natural zeolite. Depending on the results of the analysis, the steps for synthesis may be repeated to obtain the desired NSEBC product.

The following eleven paragraphs relax the simplifying assumptions previously made in this disclosure.

Within this disclosure, the chopped burdock root was used as a bio-reducing agent, or more formally, a phytochemical based reducing agent. In the preferred method of preparation of the filter medias described by this disclosure, a bio-reduction agent is used to chemically reduce the silver in the silver nitrate solution through the transfer of electrons from the bio-reduction agent to the silver. A simplifying assumption was made that the bio-reduction agent was burdock root. The applicant now relaxes this assumption with the additional disclosures made below.

A commonly used measure of the reduction capacity of a phytochemical based reducing agent is a measure called the oxygen radical absorbance capacity (hereinafter ORAC) with units of micromoles per 100 gm. It is known in the literature that the ORAC of chopped burdock root is 6747. The applicant can further confirm that a phytochemical based reducing agent with an ORAC greater than the ORAC of chopped burdock root can be conveniently substituted for use in the preferred methods of preparation of the filter media described by this disclosure. The applicant further notes that such a phytochemical based reducing agent can be directly substituted for the chopped burdock root with a reasonable expectation that the substituted phytochemical based reducing agent will be as, if not more effective than the chopped burdock root.

A list of such phytochemical based reducing agents includes, but is not limited to, chopped triphala (ORAC 706,250), chopped cloves (ORAC 290,283), dried oregano (ORAC 175,295), dried rosemary (ORAC 165,280), chaga mushroom extract (ORAC 146,700), ground cinnamon (ORAC 131,420), and chopped black cohosh root (ORAC 126,495). A phytochemical based reducing agent selected from the above list that does not include the term "chopped," does not necessarily have to be chopped before incorporation into the preferred method of preparation of the filter medias described above.

Any bio-reducing agents listed in the prior paragraph can be substituted for burdock root on a gram for gram basis. The applicant notes that the substitution of a phytochemical based bio-reducing agent with an ORAC higher than burdock root will result in a more stable, consistent, and durability of the embedded nanoparticles of a noble metal selected from the group consisting of silver (Ag) and gold (Au). Specifically, the stability, the consistency, and the durability of the embedded nanoparticles of a noble metal selected from the group consisting of silver (Ag) and gold (Au) are positive functions of the ORAC of the selected bio-reducing agent.

The applicant further observes that in an alternate method of preparation of the filter medias described involved organometallic methods requiring organic reducing agents. In this organometallic method, the organic reducing age acts as an electron donor that chemically reduces the silver in the silver nitrate solution. A simplifying assumption was made that the organic reducing agents was a sugar acid. The applicant now relaxes this assumption.

Specifically, the applicant will note that any water soluble organic acid with a dissociation constant (Ka) greater than the sugar acids described in this disclosure (approximately 12) can be substituted for any organic reducing agent described in this disclosure on a gram-mole per gram-mole (or molar) basis.

The applicant further observes that a simplifying assumption regarding the use of silver was made in the methods of preparation for the filter media. The applicant would observe that the use of nanoparticles of embedded noble metals selected from the group consisting of silver (Ag) and gold (Au) was called for in the specification and that the use of silver (Ag) was then assumed for purposes of simplicity and clarity. The applicant now relaxes this assumption.

Specifically, the applicant notes that auric nitrate (Au(NO3)3 CAS 13464-77-2) can be substituted for the silver nitrate (AgNO3 CAS 7761-88-8) described in this disclosure on a gram-mole per gram-mole (or molar) basis. This substitution is also not affected by the selection of the selection of any bio-reducing agent. This substitution is not affected by the selection of the organic reducing agent.

Consistent with the above paragraph, the substitution of auric nitrate for silver nitrate will result: 1) in the creation of nanogold embedded activated carbon (NGEAC) in lieu of nanosilver embedded activated carbon (NSEAC); 2) in the creation of nanogold embedded bone char (NGEBC) in lieu of nanosilver embedded bone char (NSEBC); and, 3) in the creation of nanogold embedded natural zeolite (NGENZ) in lieu of nanosilver embedded natural zeolite (NSENZ).

The applicant will finally note that both the auric nitrate and the silver nitrate are salts that used as vehicles to provide the noble metal that forms the nanoparticles of embedded noble metals in the filtering medium. The applicant notes that other water soluble auric salts and silver salts can be substituted for both the auric nitrate or the silver nitrate described in this disclosure on a gram-mole per gram-mole (or molar) basis.

The engineered media (NSEAC, NSENZ, NSEBC, NGEAC, NGENZ, and NGEBC) prepared in this disclosure is applicable only for ex-situ mode of treatment. The medias are not applicable for in-situ mode of treatment.

The following two paragraphs further identify the chemicals described in this disclosure.

The activated carbon has a CAS identification number of 7440-44-0. The arctiin has a CAS identification number of 20362-31-6. The arsenic has a CAS identification number of 7440-38-2. The ascorbic acid has a CAS identification number of 51-81-17. The auric nitrate has a CAS identification number of CAS 13464-77-2. The bisphenol has a CAS identification number of 80-05-7. The Bis-Phthalate has a CAS identification number of 117-81-2. The cadmium has a CAS identification number of 7440-43-9. The carbon has a CAS identification number of 7440-44-0. The chabazite has a CAS identification number of 12251-32-0. The clinoptilolite has a CAS identification number of 12173-10-3. The copper has a CAS identification number of 7440-50-8. The DDT has a CAS identification number of 50-29-3. The dioxin (1,2) has a CAS identification number of 289-87-2. The dioxin (1,4) has a CAS identification number of 290-67-5.

The fluorine has a CAS identification number of 7782-41-4. The glucaric acid has a CAS identification number of CAS 87-73-0. The gluconic acid has a CAS identification number of CAS 526-95-4. The glyceric acid has a CAS identification number of CAS 473-81-4. The inulin has a CAS identification number of 9005-80-5. The lead has a CAS identification number of 7439-92-1. The mercury has a CAS identification number of 7439-97-6. The mordenite has a CAS identification number of 12173-98-7. The nitrate has a CAS identification number of 14797-55-8. The perchloroethylene has a CAS identification number of 127-18-4. The radium has a CAS identification number of 7440-14-4. The silver has a CAS identification number of 7440-22-4. The silver nitrate has a CAS identification number of CAS 7761-88-8. The trichloroethylene has a CAS identification number of 79-01-6. The uranium has a CAS identification number of 7440-61-1. The zinc has a CAS identification number of 7440-66-6.

The following definitions, acronyms, and references were used in this disclosure:

Bone Char: As used in this disclosure, bone char is an activated material that is produced by charring, usually through pyrolysis, animal bones. The bone char thereafter is activated by the injection of steam and oxygen.

Burdock: As used in this disclosure, burdock is a perennial plant found in the United States, China, and Europe Cancellated: As used in this disclosure, cancellated is used as an adjective to describe a sponge like, net like, or screen like structure.

CBR: As used in this disclosure, CBR is an acronym for chopped burdock root.

Column: As used in this disclosure, a column is a hollow device that is used for processing and transporting liquids and gasses.

Cross-section: As used in this disclosure, a cross-section is a surface or shape that would be exposed by making a straight cut through an object.

Drinking Water: As used in this disclosure, drinking water is water that is deemed safe for drinking or use in cooking. A synonym is potable water.

Inner Diameter: As used in this disclosure, the term inner diameter is used in the same way that a plumber would refer to the inner diameter of a pipe.

Mesh: As used in this disclosure, the term mesh refers to a measure of the size of particle a screen or sieve will pass. Specifically, mesh refers to the number of holes per linear inch of the screen or sieve surface. For example, a sieve surface with ten holes per linear inch is referred to as 10 mesh. A ten mesh screen or sieve surface will have on average 100 holes per square inch.

NSEAC: As used in this disclosure, NSEAC is an acronym for nanosilver embedded activated carbon.

NSEBC: As used in this disclosure, NSEBC is an acronym for nanosilver embedded activated bone char.

NSENZ: As used in this disclosure, NSENZ is an acronym for nanosilver embedded natural zeolite.

NGEAC: As used in this disclosure, NSEAC is an acronym for nanogold embedded activated carbon.

NGEBC: As used in this disclosure, NSEBC is an acronym for nanogold embedded activated bone char.

NGENZ: As used in this disclosure, NSENZ is an acronym for nanogold embedded natural zeolite.

ORAC: As used in this disclosure, ORAC is an acronym for oxygen radical absorbance capacity is a standard measure used to compare the effectiveness of bio reducing agents.

Pharmacologically Active Media: As used in this disclosure, a pharmacologically active media refers to a chemical substance that has a biochemical or physiological effect on a biological organism.

Phytochemical: As used in this disclosure, a phytochemical is a pharmacologically active media that is produced in and harvested from a plant.

Reduction Oxidation Reaction: As used in this disclosure, a reduction oxidation reaction (also known as a redox reaction) is a chemical reaction involving the transfer of electrons between the reactants of the reaction.

Salt: As used in this disclosure, a salt means an ionic compound that further comprises at least one atom of a metallic element or compound and one atom of a non-metallic element or compound. When dissolved in water, the ionic compound releases the metallic element and the non-metallic element into the water as ions. In this disclosure, a metallic element is assumed to include the alkali metals and the alkali earth metals. Alternatively, and equivalently, a metallic element may be assumed to be any element on the periodic table that is to the left of the metalloids.

Untreated Water: As used in this disclosure, untreated water is water that has not been completely processed by the invention described in this disclosure.

Webbing: As used in this disclosure, a webbing is strong, close woven fabric that is used for straps or belting.

Zeolite: As used in this disclosure, a zeolite is any of a group of anhydrous aluminum silicate, or their corresponding synthetic compounds, that are used as molecular filters and ion exchange agents The following drinking water quality standards are referenced in this disclosure:

United States Drinking Water Quality Standard: United States EPA 816-F-09-004. May 2009

United States Bottled Drinking Water Quality Standard: US 21 CFR 165 110 (b) Apr. 1, 2013.

World Health Organization Drinking Water Quality Standard: WHO Guidelines for Drinking Water Quality 4$^{th}$ Edition, 2011.

European Union Drinking Water Quality Standard: European Union Drinking Water Directive Council Directive 98/83/EC Nov. 3, 1998.

With respect to the above description, it is to be realized that the optimum dimensional relationship for the various components of the invention described above and in FIGS. 1 through 3, include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

What is claimed is:

1. A method for creating an engineered media comprising a noble metal salt solution, a substrate media, and a bio-reducing agent solution;
   wherein the noble metal is selected from the group consisting of silver and gold;
   wherein a mixture of the substrate media and the noble metal salt solution forms a first slurry;
   wherein a mixture of the bio-reducing agent solution and the first slurry forms a second slurry;
   wherein the second slurry creates a nanoparticle embedded substrate media;
   wherein by nanoparticle embedded substrate media is meant: a) a plurality of particles of the selected noble metal are incorporated into the matrix formed by the substrate medium, and, b) the plurality of incorporated particles have an average diameter of less than or equal to 5 nm;
   wherein the nanoparticle embedded substrate media is removed from the second slurry;
   wherein the nanoparticle embedded substrate media is rinsed;
   wherein the nanoparticle embedded substrate media is dried;
   wherein the bio-reducing agent solution is an extract of a phytochemical based bio-reducing agent;
   wherein the second slurry chemically reduces the noble metal contained in the noble metal salt solution;
   wherein the second slurry reduces the noble metal to nanoparticle size;
   wherein the second slurry embeds the nanoparticles of the noble metal into the substrate media;
   wherein the engineered media is applicable only for an ex-situ mode of treatment.

2. The method for creating an engineered media according to claim 1
   wherein the first slurry is tumbled for a first period of time;
   wherein the second slurry is tumbled for a second period of time;
   wherein, after the completion of the second period of time, the second slurry is maintained in darkness for a third period of time;
   wherein the nanoparticles of the noble metal embedded substrate media are rinsed using water;
   wherein the nanoparticles of the noble metal embedded substrate media are dried in a vacuum.

3. The method for creating an engineered media according to claim 2
   wherein the noble metal salt solution is a 1 Molar solution of the noble metal salt in water;
   wherein the method for creating an engineered media further comprises a fourth period of time;
   wherein the fourth period of time is greater than or equal to three hours;
   wherein the first period of time is greater than or equal to three-quarters of an hour;
   wherein the second period of time is greater than or equal to two and one-half hours;
   wherein the third period of time is greater than or equal to nineteen hours.

4. The method for creating an engineered media according to claim 3
   wherein the phytochemical based bio-reducing agent is a chopped burdock root;
   wherein burdock root is chopped to form the chopped burdock root such that the chopped burdock root has an average particle span of less than 5 mm;
   wherein the chopped burdock root is placed in water to form a chopped burdock root slurry;
   wherein the chopped burdock root slurry is maintained at a temperature between 55 C and 75 C for a fourth period of time;
   wherein, after the completion of the fourth period of time, the chopped burdock root is removed from the chopped burdock root slurry;
   wherein the liquid remaining after the removal of the chopped burdock root is the chopped burdock root extract;
   wherein the chopped burdock root slurry is formed in a ratio of 200 gm chopped burdock root per 1 L of water;
   wherein the chopped burdock root extract is the phytochemical based bio-reducing agent solution.

5. The method for creating an engineered media according to claim 4 wherein the substrate media is activated carbon.

6. The method for creating an engineered media according to claim 4
wherein the substrate media is a natural zeolite;
wherein the natural zeolite is selected from the group consisting of chabazite (CAS 12251-32-0), clinoptilolite (CAS 12173-10-3), and mordenite (CAS12173-98-7).

7. The method for creating an engineered media according to 4 wherein the substrate media is an activated bone char.

8. The method for creating an engineered media according to claim 3
wherein the phytochemical based bio-reducing agent is further defined with an ORAC value;
wherein the phytochemical based bio-reducing agent is chopped such that the phytochemical based bio-reducing agent has an average particle span of less than 5 mm;
wherein the phytochemical based bio-reducing agent is placed in water to form a reducing slurry;
wherein the reducing slurry is maintained at a temperature between 55 C and 75 C for a fourth period of time;
wherein, after the completion of the fourth period of time, the phytochemical based bio-reducing agent root is removed from the reducing slurry;
wherein the liquid remaining after the removal of the phytochemical based bio-reducing agent is the reducing slurry extract;
wherein the reducing slurry extract is formed in a ratio of 200 gm of phytochemical based bio-reducing agent per 1 L of water;
wherein the reducing slurry extract is the bio-reducing agent solution.

9. The method for creating an engineered media according to claim 8
wherein the stability of the embedded nanoparticles of the noble metal selected from the group consisting of silver (Ag) and gold (Au) is a positive function of the ORAC of the selected bio-reducing agent;
wherein the consistency of the embedded nanoparticles of the noble metal selected from the group consisting of silver (Ag) and gold (Au) is a positive function of the ORAC of the selected bio-reducing agent;
wherein durability of the embedded nanoparticles of the noble metal selected from the group consisting of silver (Ag) and gold (Au) is a positive function of the ORAC of the selected bio-reducing agent.

10. The method for creating an engineered media according to claim 9
wherein the phytochemical based bio-reducing agent has an ORAC value of greater than 100,000;
wherein the phytochemical based bio-reducing agent is selected from the group consisting of chopped triphala, chopped cloves, dried oregano, dried rosemary, chaga mushroom extract, ground cinnamon, and chopped black cohosh root.

11. The method for creating an engineered media according to claim 10 wherein the substrate media is activated carbon.

12. The method for creating an engineered media according to claim 10
wherein the substrate media is a natural zeolite;
wherein the natural zeolite is selected from the group consisting of chabazite (CAS 12251-32-0), clinoptilolite (CAS 12173-10-3), and mordenite (CAS12173-98-7).

13. The method for creating an engineered media according to claim 10 wherein the substrate media is an activated bone char.

14. A method for creating an engineered media comprising
a noble metal salt solution, a substrate media, and an organic reducing agent;
wherein the noble metal is selected from the group consisting of silver and gold;
wherein the organic reducing agent is dissolved in the noble metal salt solution to form a first solution;
wherein a mixture of the substrate media and the first solution forms a first slurry;
wherein the first slurry creates a partially embedded substrate media;
wherein the partially embedded substrate media is removed from the first slurry;
wherein the partially embedded substrate media is rinsed;
wherein the partially embedded substrate media is pyrolyzed to form a nanoparticle embedded substrate media;
wherein by nanoparticle embedded substrate media is meant: a) a plurality of particles of the selected noble metal are incorporated into the matrix formed by the substrate medium, and, b) the plurality of incorporated particles have with an average diameter of less than or equal to 5 nm;
wherein the first slurry is tumbled for a first period of time to form the partially embedded substrate material;
wherein the partially embedded substrate material is rinsed using deionized water;
wherein the nanoparticle embedded substrate media is created by pyrolyzing the partially embedded substrate material is in a vacuum at 250 C for a second period of time;
wherein the engineered media is applicable only for an ex-situ mode of treatment;
wherein the noble metal salt solution is a 1 Molar solution of noble metal salt in water;
wherein the first period of time is greater than two and one-half hours;
wherein the second period of time is greater than one and one-half hours;
wherein the organic reducing agent is a sugar acid.

15. The method for creating an engineered media according to claim 14 wherein the substrate media is activated carbon.

16. The method for creating an engineered media according to claim 15 wherein the sugar acid is selected from the group consisting of glucaric acid, gluconic acid, and glyceric acid, ascorbic acid, a sugar acid of the ulosonic acid family, a sugar acid of the uronic acid family, and a sugar acid of the aldaric acid family.

17. The method for creating an engineered media according to claim 14
wherein the substrate media is a natural zeolite;
wherein the natural zeolite is selected from the group consisting of chabazite (CAS 12251-32-0), clinoptilolite (CAS 12173-10-3), and mordenite (CAS12173-98-7).

18. The method for creating an engineered media according to claim 17 wherein the sugar acid is selected from the group consisting of glucaric acid, gluconic acid, and glyceric acid, ascorbic acid, a sugar acid of the ulosonic acid family, a sugar acid of the uronic acid family, and a sugar acid of the aldaric acid family.

19. The method for creating an engineered media according to claim 14 wherein the substrate media is an activated bone char.

20. The method for creating an engineered media according to claim 19 wherein the sugar acid is selected from the group consisting of glucaric acid, gluconic acid, and glyceric acid, ascorbic acid, a sugar acid of the ulosonic acid family, a sugar acid of the uronic acid family, and a sugar acid of the aldaric acid family.

* * * * *